United States Patent
Aramata et al.

(10) Patent No.: US 7,521,574 B2
(45) Date of Patent: Apr. 21, 2009

(54) MAKING OF CONTACT MASS FOR ORGANOHALOSILANE PREPARATION AND PREPARATION OF ORGANOHALOSILANES

(75) Inventors: Mikio Aramata, Gunma-ken (JP); Hajime Ishizaka, Annaka (JP); Tetsuya Inukai, Annaka (JP); Kenji Saito, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 11/251,862

(22) Filed: Oct. 18, 2005

(65) Prior Publication Data

US 2006/0084821 A1   Apr. 20, 2006

(30) Foreign Application Priority Data

Oct. 19, 2004   (JP) ............................. 2004-304223

(51) Int. Cl.
    *C07F 7/16*   (2006.01)
(52) U.S. Cl. ....................................... 556/472; 423/342
(58) Field of Classification Search ................. 556/472; 423/342
    See application file for complete search history.

(56) References Cited

U.S. PATENT DOCUMENTS

| 2,380,995 A | | 8/1945 | Rochow et al. |
|---|---|---|---|
| 4,500,724 A | | 2/1985 | Ward, III et al. |
| 5,756,794 A | * | 5/1998 | Steiner et al. ................ 556/472 |
| 6,090,966 A | * | 7/2000 | Nakanishi et al. ............ 556/472 |
| 6,156,380 A | * | 12/2000 | Aramata et al. ............. 427/217 |
| 6,258,970 B1 | * | 7/2001 | Ward et al. ................... 556/472 |
| 6,528,674 B1 | * | 3/2003 | Lewis et al. .................. 556/472 |
| 2003/0220514 A1 | * | 11/2003 | Lewis et al. .................. 556/473 |
| 2005/0043557 A1 | | 2/2005 | Aramata et al. |

FOREIGN PATENT DOCUMENTS

| EP | 1 508 571 A1 | 2/2005 |
|---|---|---|
| JP | 32-4570 B | 7/1932 |
| JP | 33-1370 B | 2/1933 |
| JP | 1-40035 B | 8/1989 |
| JP | 2005-97249 A | 4/2005 |

OTHER PUBLICATIONS

Eugene G. Rochow, J. Am. Chem. Soc., 67, pp. 963-965, (1945), "The direct synthesis of organosilicon compounds."
Eugene G. Rochow et al., J. Am. Chem. Soc., 67, pp. 1772-1775, (1945), "The direct synthesis of phenylchlorosilanes."

* cited by examiner

*Primary Examiner*—Daniel M Sullivan
*Assistant Examiner*—Chukwuma O Nwaonicha
(74) *Attorney, Agent, or Firm*—Birch, Stewart, Kolasch & Birch, LLP

(57) ABSTRACT

Organohalosilanes are prepared by charging a reactor with a contact mass comprising metallic silicon and a catalyst and feeding an organohalide-containing gas to the reactor. The contact mass is prepared by premixing metallic silicon and a tin compound and heat treating the premix at 300-600° C. in an inert gas atmosphere.

9 Claims, 2 Drawing Sheets

MAKING OF CONTACT MASS FOR ORGANOHALOSILANE PREPARATION AND PREPARATION OF ORGANOHALOSILANES

CROSS-REFERENCE TO RELATED APPLICATION

This non-provisional application claims priority under 35 U.S.C. §119(a) on Patent Application No. 2004-304223 filed in Japan on Oct. 19, 2004, the entire contents of which are hereby incorporated by reference.

TECHNICAL FIELD

This invention generally relates to a direct process for preparing organohalosilanes, and more particularly, to a direct process for continuously preparing organohalosilanes through gas-solid catalytic reaction using tin compounds as a main catalyst instead of conventional copper catalysts. It also relates to a method of preparing a contact mass, especially tin-silicon contact mass for use in the preparation of organohalosilanes by the direct process.

BACKGROUND ART

With respect to the synthesis of organohalosilanes, E. G. Rochow first disclosed direct reaction between metallic silicon and organohalide in the presence of a copper catalyst. See U.S. Pat. No. 2,380,995 and J. Am. Chem. Soc., 67, 963 (1945), "The direct synthesis of organosilicon compounds." Further, J. Am. Chem. Soc., 67, 1772 (1945), "The direct synthesis of phenylchlorosilanes" reports that the contact mass is useful in the synthesis of phenylsilanes. After these reports, copper catalysts are acknowledged as prevailing catalysts in the organohalosilane synthesis by direct reaction of metallic silicon with organohalide. Since then, there have been reported a number of research works relating to various co-catalysts used together with copper catalysts, copper catalysts themselves and their treatment, reactors, additives used during reaction, and the like. All prior art investigations relate to copper catalyzed reactions.

On the other hand, tin serves as a catalyst in the contact mass for organohalosilane direct synthesis reaction, but in fact, tin is used solely as a co-catalyst for promoting reaction when copper is used as the main catalyst. For instance, U.S. Pat. No. 4,500,724 and JP-B 1-40035 disclose use of tin for methylhalosilane synthesis, JP-B 33-1370 discloses tin or tin alloys for phenylsilane synthesis, and JP-B 32-4570 discloses tin tetrahalides. No reference has been made to the contact masses in which the copper catalyst is absent or the copper catalyst is present in minor amounts, but not used as the main catalyst.

No substantial problems have arisen as long as the reaction deals with only methylhalosilanes. As silicone resins become diversified, there is an increasing demand for organohalosilanes having other organic groups such as phenyl. Synthesis of such organohalosilanes is carried out, as a matter of course, by direct reaction of metallic silicon with chlorobenzene in the presence of copper catalysts. The reaction with such organohalides having low reactivity suffers from the problems that the reaction temperature must be elevated (to about 400 to 600° C.), large amounts of by-products such as biphenyls and carbon form to complicate post-treatment, and the percent conversion of silicon to silane is very low despite a very large amount of the catalyst used.

SUMMARY OF THE INVENTION

An object of the invention is to provide a simple, industrially acceptable method for preparing a contact mass for silane synthesis which contains tin as a main catalyst, but not copper or copper compounds which have been considered essential as a main catalyst in the direct or Rochow process; and a process for preparing organohalosilanes using the contact mass having a high activity and causing minimal side reaction.

Addressing a process for direct synthesis of organohalosilanes by reaction of organohalides having low reactivity with metallic silicon, e.g., a process for preparing organohalosilanes by industrially advantageous direct reaction of chlorobenzene with metallic silicon, the inventors discovered a novel contact mass using tin or a tin compound as a main catalyst instead of copper (see JP-A 2005-97249 or US 2005-0043557). Better results are obtained by adding tin or a tin compound to metallic silicon powder, preferably in an amount of 0.01 to 50% by weight based on the weight of the silicon powder, intimately mixing them, and using the resulting mixture as a contact mass for the above-described reaction. As compared with the conventional contact mass using copper as the main catalyst, this contact mass is effective in maintaining at least equal reactivity, improving the composition of organohalosilanes, especially diorganodihalosilane, and significantly reducing formation of biphenyl and carbonaceous by-products during phenylhalosilane synthesis. As a result, the percent conversion of silicon is drastically increased.

Partly because it is difficult to form an alloy of tin-silicon system, the tin-silicon contact mass is prepared by mechanically mixing tin or tin compound and silicon. The preparation of such an active tin-silicon contact mass resorts to the mechanical fusion of tin to metallic silicon, which leaves some problems with respect to scale-up manufacture or the like. There exists a need to establish an industrially acceptable method for the preparation of the contact mass. The inventors have discovered that by premixing a tin compound with a silicon powder thoroughly and heat treating the premix in an inert gas stream, a contact mass for organohalosilane synthesis having a high activity and causing minimal side reaction can be prepared in a simple, industrially acceptable, inexpensive manner and in a mass scale.

The present invention provides a method for preparing a contact mass for use in the preparation of organohalosilanes, comprising the steps of premixing metallic silicon and a tin compound, and heat treating the premix in an inert gas atmosphere.

In another aspect, the present invention provides a process of preparing organohalosilanes, comprising the steps of charging a reactor with a contact mass comprising metallic silicon and a catalyst and feeding an organohalide-containing gas to the reactor, the contact mass being prepared by premixing metallic silicon and a tin compound and heat treating the premix in an inert gas atmosphere. The organohalosilanes have the general formula (1):

$$R_n H_m SiX_{(4-n-m)} \qquad (1)$$

wherein R is a monovalent hydrocarbon group, X is a halogen atom, n is an integer of 1 to 3, m is an integer of 0 or 1, and the sum of n+m is 1 to 3.

The tin catalyst (tin compound) is preferably a tin halide, tin nitrate, tin sulfate, or tin organic acid salt. The tin compound is preferably added in an amount to provide 0.01 to 50 parts by weight of metallic tin per 100 parts by weight of metallic silicon. Typically in the process of the invention, phenylchlorosilanes are prepared using phenyl chloride as the organohalide.

The present invention enables to prepare a tin-silicon contact mass for organohalosilane synthesis in a simple, industrially acceptable manner. The contact mass is used in the preparation of organohalosilanes at a high reaction rate. Then, the organohalosilanes can be produced quite efficiently while maintaining a low T/D ratio and minimizing the deposition of by-products and carbon. Here T represents organotrihalosilane and D represents diorganodihalosilane, and a low T/D means a good selectivity of useful organohalosilane.

DESCRIPTION OF THE PREFERRED EMBODIMENTS

Figure 1:
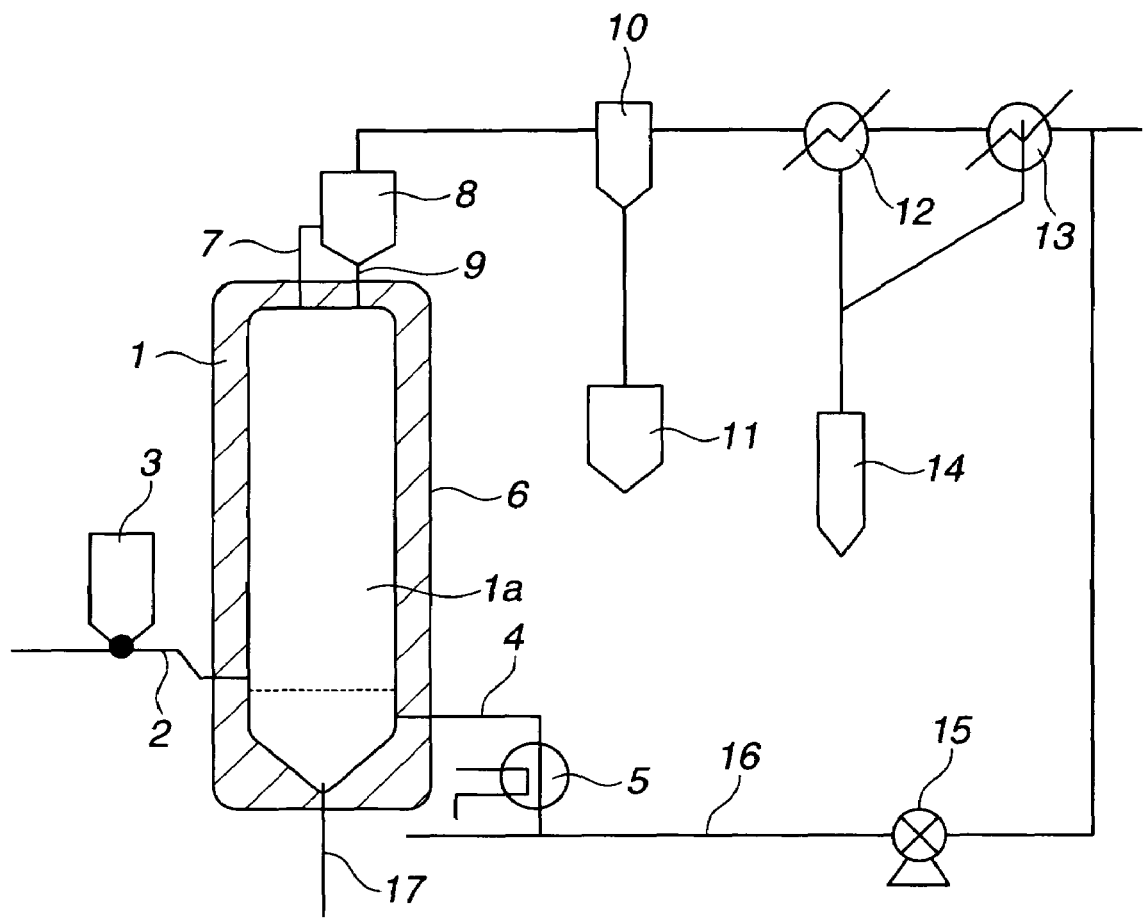
FIG. 1 schematically illustrates a preparation apparatus used in the practice of the invention.

The present invention pertains to both a method of preparing a contact mass and a process of preparing organohalosilanes using the contact mass. The process of preparing organohalosilanes involves the steps of charging a reactor with a contact mass comprising metallic silicon and a catalyst and feeding an organohalide-containing gas to the reactor. The organohalosilanes have the general formula (1):

  (1)

$$R_n H_m SiX_{(4-n-m)}$$

wherein R is a monovalent hydrocarbon group, X is a halogen atom, n is an integer of 1 to 3, m is an integer of 0 or 1, and the sum of n+m is 1 to 3. The contact mass is prepared by premixing metallic silicon and a tin compound and heat treating the premix in an inert gas atmosphere. Once the reactor is charged with the contact mass, an organohalide-containing gas is fed to the reactor and brought into contact with the contact mass, thereby forming organohalosilanes.

The metallic silicon used herein preferably has a silicon purity of at least 97% by weight, especially at least 98% by weight. Prior to use, the metallic silicon is preferably ground into particles with an appropriate particle size. Where the reactor used is a fluidized bed or stirred bed reactor, the metallic silicon powder should preferably have a particle size in the range of 10 to 100 µm, more preferably 20 to 80 µm, corresponding to 50% of the weight-base cumulative size distribution curve on sieving.

The tin catalyst used herein is selected from tin compounds of various types, for example, tin halides, tin nitrate, tin sulfate, tin organic acid salts and mixtures thereof. Of these, tin halides such as tin chloride are preferred. In the tin compounds, tin may be divalent or tetravalent. Suitable tin compounds are commercially available.

The tin compound in powder form should preferably have an average particle size in the range of 1 to 200 µm, more preferably 1 to 75 µm, even more preferably 1 to 50 µm, most preferably 1 to 30 µm, corresponding to 50% of the weight-base cumulative size distribution curve on sieving. With too small an average particle size, only a few particles may attach to surfaces of metallic silicon particles and many particles may scatter out of the reactor during activation, failing to exert the desired effect. Tin compound particles with too large an average particle size may contact with metallic silicon particles ineffectively and detract from the chemical reduction and dispersity of the tin compound in the contact mass-forming step.

An appropriate amount of the tin catalyst added is 0.01 to 50 parts by weight, more preferably 0.1 to 5 parts by weight, calculated as metallic tin, per 100 parts by weight of metallic silicon. Too small an amount of the tin catalyst may fail to achieve the desired effect to a full extent whereas too large an amount may allow tin to precipitate as liquid in the reaction system, incurring disordered flow or poor contact.

In the inventive method, metallic silicon and the tin compound are premixed to form a premix or precursor, which is heat treated to form a contact mass. The mixing technique is not critical, and an apparatus commonly used in powder mixing or mixer may be used. Exemplary mixing techniques include a technique of dispersing metallic silicon powder and the tin compound in a non-polar solvent for attaching the tin compound to surfaces of metallic silicon particles, and drying; another technique of dissolving the tin compound in a good solvent such as water, mixing the solution with metallic silicon powder, and drying; and a further technique of mixing metallic silicon and the tin compound under substantial shear forces (specifically, metallic silicon and the tin compound are rubbed together in a mortar or the like, and in a preferred industrial practice, metallic silicon and the tin compound are rubbed together by mechanically applying high shear forces in a non-oxidizing atmosphere). Any of these techniques may be employed.

Heat treatment is carried out by feeding the precursor to a reactor, flowing an inert gas through the reactor until the reactor is fully purged therewith, and heating the precursor. In the preparation of tin-silicon contact mass from the contact mass precursor, the inert gas which is flowed for the purging of the reactor and/or the removal of product silane is typically nitrogen gas, argon gas or the like, with the use of nitrogen gas being desired from the economic aspect. After the purging, the flow velocity of the inert gas in these steps is preferably at a level enough to remove the product silane. At too high a flow velocity of the inert gas, a substantial loss occurs since a tin halide or tin compound having a high vapor pressure, in particular, will volatilize off the system. It is recommended to recycle the inert gas after separation of the product silane.

The heating conditions may be determined as appropriate in accordance with the size of the reactor, the linear velocity of inert gas, and other factors. The heating temperature is preferably in a range of 300 to 600° C., more preferably 350 to 500° C. The heating time is preferably from 1 to 10 hours, more preferably from 2 to 4 hours. Below these ranges, the tin compound may undergo insufficient chemical reduction. Conditions beyond these ranges may lead to an energy loss.

The above-described method converts the tin compound added to an active state capable of exerting catalysis, achieving a significant increase in the activity of phenylchlorosilane synthesis reaction.

With the above-described method, the tin or tin compound is dispersed and deposited onto surfaces of metallic silicon particles. Specifically, the tin or tin compound is deposited on surfaces of metallic silicon particles in the state that fractured particles, flake particles, hemispherical or hemi-ellipsoidal particles or otherwise shaped particles of the tin or tin compound are dispersed as groups of islands or a plurality of discrete islands. The tin or tin compound deposits or islands preferably have a thickness or height of up to 20 µm, more preferably up to 15 µm, as observed under a microscope.

Reference is now made to an example where tin chloride ($SnCl_2$) is used as the tin compound. On heating, the following reaction takes place.

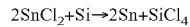

$$2SnCl_2 + Si \rightarrow 2Sn + SiCl_4$$

Sn ties with metallic silicon as Si—Sn to manifest a significant catalysis. Herein, Si and Sn may or may not form a chemical bond. $SiCl_4$ is carried out of the system by the flowing inert gas. The contact mass of metallic silicon and tin or tin compound combined in this way is used in the synthesis of phenylchlorosilanes by direct reaction, thereby achieving a very high productivity without substantially increasing the formation of benzene and biphenyl by-products.

To the reaction system, promoters such as zinc, antimony, arsenic and phosphor and compounds and alloys thereof which are used as the co-catalyst in the current silane synthesis reaction, and agents for improving the selectivity of organotrihalosilane, such as iron, aluminum, and halides thereof may be added, and even trichlorosilane may be added as well. It is not critical whether or not these agents are added. It is not necessarily needed to add copper and alloys and compounds thereof which are generally used in the Rochow reaction. An appropriate amount of these co-catalysts added is 0 to 20 parts by weight, more preferably 0.05 to 5 parts by weight, calculated as the total of co-catalyst metals, per 100 parts by weight of metallic silicon, but should be smaller than the amount of tin added as the tin catalyst.

No copper is essentially used. It is acceptable that copper be included as an incidental impurity in metallic silicon and the catalyst, specifically in an amount of less than 0.1% by weight, especially up to about 0.05% by weight of copper based on the metallic silicon. In phenylhalosilane synthesis, the amount of copper is limited to less than 0.1% based on metallic silicon because biphenyls are likely to form in the presence of 0.1% by weight or more of copper.

The organohalide to be reacted with metallic silicon to form organohalosilanes of the formula (1) typically has the general formula (2).

$$RX \qquad (2)$$

Herein, R is a monovalent hydrocarbon group. Suitable monovalent hydrocarbon groups are those of 1 to 12 carbon atoms, for example, aryl groups such as phenyl and tolyl, aralkyl groups such as benzyl, phenylethyl and phenylpropyl, alkenyl groups such as vinyl, allyl, propenyl and butenyl, and alkyl groups such as methyl, ethyl, propyl, butyl and hexyl. X is a halogen atom such as chlorine and bromine. Exemplary organohalides are chlorobenzene, methyl chloride, ethyl chloride, methyl bromide and ethyl bromide. Of these, chlorobenzene and methyl chloride are advantageous in the industry. Chlorobenzene or phenyl chloride is most favorable in the invention.

The organohalide is previously heated and gasified before it is admitted into the reactor. The organohalide vapor or gas may be fed alone or combined with an inert gas. The organohalide gas is fed in a sufficient amount to fluidize the contact mass together with the inert gas, the fluidizing amount being determined as appropriate from the diameter of the reactor and the superficial velocity.

In the step of heating the contact mass or imparting catalytic activity to the contact mass, an inert gas is used for fluidizing the contact mass in the reactor. Such an inert gas may be nitrogen or argon gas, for example, with the nitrogen gas being preferable from the economic standpoint. The flow velocity of the inert gas fed in this and subsequent steps is at least the minimum fluidization velocity of the contact mass, and preferably about 5 times the minimum fluidization velocity. A flow velocity of the inert gas below the range may often fail to achieve uniform fluidization of the contact mass. If the flow velocity of the inert gas is above the range, metallic silicon particles may excessively scatter away with increased losses of the inert gas and heat. It is recommended to recycle the inert gas.

The tin-silicon contact mass may be prepared either in a separate reactor from the organohalosilane-producing reactor previously or simultaneously with the organohalosilane-producing step, which is preferred from an efficiency standpoint, or in the organohalosilane-producing reactor. In either case, the reactor is charged with the tin-silicon contact mass and purged with an inert gas and heated to the reaction temperature for imparting catalytic activity to the contact mass as mentioned above, after which the organohalide is introduced into the reactor where gas-solid catalytic reaction takes place between the organohalide and metallic silicon to form organohalosilanes. The conditions for this gas-solid catalytic reaction may be the same as in the conventional Rochow process. For example, the reaction temperature may be in the range of 350 to 500° C.

Any desired apparatus may be used for the organohalosilane preparation process of the invention. FIG. 1 illustrates one exemplary preparation apparatus which includes a fluidized bed reactor 1, an input line 2 and a charge feed hopper 3. The hopper 3 contains a tin-silicon contact mass which has been prepared according to the invention, optionally in admixture with a co-catalyst. The contact mass is fed to the bottom of the reactor 1 through the line 2. In the contact mass system, tin can precipitate out with the progress of reaction and become liquid or viscous due to combination with silicon, and such liquid or viscous matter is discharged through a discharge line 17. An organohalide feed line 4 surrounded by a heater 5 is also connected to the reactor 1 at the bottom. An organohalide gas or vapor is introduced into the reactor 1 at the bottom for thereby forming a fluidized bed 1a of metallic silicon and catalyst within the reactor 1. The reactor 1 has a cooling jacket 6.

Preferably the organohalide gas or vapor is introduced at a linear velocity of 2 to 20 cm/sec in the steady state. The reaction is typically effected at a temperature of about 350 to 500° C.

The organohalosilane product resulting from the reaction flows through an output line 7 connected to the top of the reactor 1, and then into a first cyclone 8 where entrained solid particles are separated off. The solid particles are returned to the fluidized bed 1a via a solid particle return line 9. The organohalosilane then passes to a second cyclone 10 where still entrained solid particles are separated off and stored in a separated particle storage tank 11. Next, the organohalosilane is condensed in a first silane condenser or simple evaporator 12, then in a second silane condenser or simple evaporator 13, and is collected and stored in a silane storage tank 14. Some or all of the waste gas and vapor remaining after the solid particles have been separated off and the organohalosilane has been condensed and removed is returned once again to the reactor 1 through an organohalide return line 16 equipped with a circulating pump (or circulating gas compressor) 15. The return line 16 is connected to the organohalide feed line 4. A fluidized bed reactor is used in the illustrated embodiment although a stirred bed reactor, a fixed bed reactor or the like may also be used.

The process of the invention is carried out as above to produce organohalosilanes having the general formula (1):

$$R_nH_mSiX_{(4-n-m)} \qquad (1)$$

wherein R is a monovalent hydrocarbon group as defined above, X is a halogen atom, n is an integer of 1 to 3, m is an integer of 0 or 1, and the sum of n+m is an integer of 1 to 3. It is preferred from the demand balance that m have an average value of approximately 0 and n have an average value of approximately 1 to 2. Then the product contain a large proportion, typically 50 to 95%, of a diorganodihalosilane (D) (wherein n=2 and m=0) which is most useful as a silicone-forming reactant while the amount of organotrihalosilane (T) (wherein m=0) formed is minimized. Particularly under ideal reaction conditions that avoid contact with a Lewis acid such as ferric chloride, the T/D ratio may be typically up to 0.3, and especially up to 0.1. At the same time, formation of biphenyls as by-products in the reaction of chlorobenzene with metallic silicon is minimized. The amount of such by-products is typically reduced to 1/10 or less, as compared with the conventional reaction processes using copper base catalysts.

EXAMPLE

Examples of the invention are given below by way of illustration and not by way of limitation. All parts and percents are by weight. The average particle size was measured as described above.

Example 1

Chemical grade metallic silicon powder having an average particle size of 50 μm (by Simcoa, low aluminum grade: Al 0.05%, Fe 0.23%, Ca 0.02%), 100 g, was weighed and placed in a polyethylene bag, to which was added 5 g of previously finely divided stannous chloride having an average particle size of 20 μm. The contents were thoroughly mixed. The tin-silicon precursor thus obtained was placed in a half-cut quartz boat having an outer diameter of 75 mm, which was closed with a quartz boat of the same size. The assembly was placed in a quartz tube having an inner diameter of about 80 mm, through which nitrogen gas was flowed for purging the interior with nitrogen. Thereafter, the quartz tube was heated to 500° C. and held for about 2 hours for reaction, obtaining a contact mass. In the course of heating, the occurrence of reducing reaction of the tin compound was confirmed by the formation of tetrachlorosilane. Table 1 shows the results of analysis on the tin-silicon precursor and contact mass.

TABLE 1

|  | Sn (wt %) | Cl (wt %) |
|---|---|---|
| Tin-silicon precursor | 2.8 | 1.9 |
| Contact mass | 2.6 | 0.02 |

Figure 2:
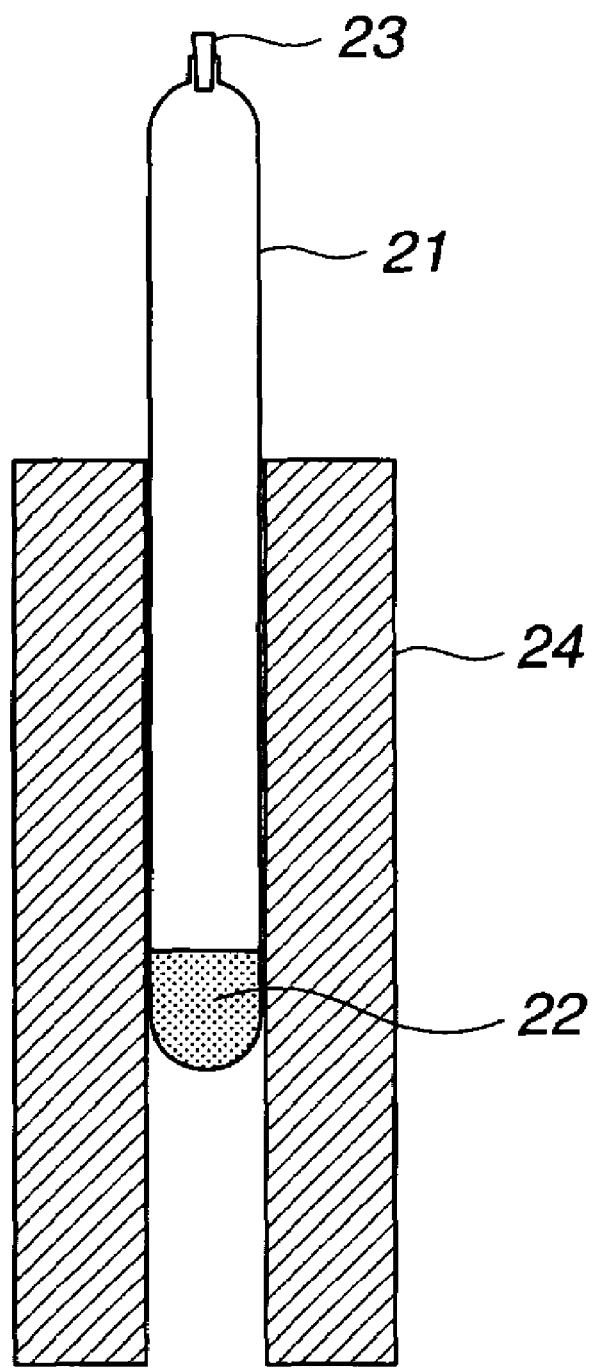
FIG. 2 schematically illustrates an experimental setup used in Example 1 and Comparative Examples 1 and 2.

An experiment was carried out using the tin-silicon contact mass and an experimental setup as shown in FIG. 2. A Pyrex® glass tube 21 having an interior volume of 25 ml was furnished. The contact mass 22 (1.0 g) was placed in the tube 21, which was closed with a silicone rubber plug 23. Using a vacuum pump, the tube was evacuated to a vacuum of lower than 0.1 Torr. Through the rubber plug 23, 0.1 ml (0.11 g) of chlorobenzene was injected into the tube. The tube 21 was heated at 450° C. for one hour in a ring furnace 24 and then allowed to cool down. Then 5 ml of chloroform containing 1% methanol (simply referred to as chloroform, hereinafter) was injected, followed by 10 minutes of shaking. The interior was restored to atmospheric pressure. The reaction solution diluted with chloroform was filtered and quantitatively analyzed by gas chromatography. Table 2 shows reaction product species and their quantities.

Comparative Example 1

An experiment was carried out using an experimental setup as shown in FIG. 2. A Pyrex® glass tube 21 having an interior volume of 25 ml was furnished. A contact mass was prepared by combining 10 g of chemical grade metallic silicon powder having an average particle size of 150 μm with 1.0 g of flaky tin powder having an average particle size of 75 μm and thoroughly mixing in an agate mortar to form a mixture (contact mass). The contact mass 22 (1.5 g) was placed in the tube 21, which was closed with a silicone rubber plug 23. Using a vacuum pump, the tube was evacuated to a vacuum of lower than 0.1 Torr. Through the rubber plug 23, 0.1 ml (0.11 g) of chlorobenzene was injected into the tube. The tube 21 was heated at 450° C. for one hour in a ring furnace 24 and then allowed to cool down. Then 5 ml of chloroform was injected, followed by 10 minutes of shaking. The interior was restored to atmospheric pressure. The reaction solution diluted with chloroform was filtered and quantitatively analyzed by gas chromatography. Table 2 shows reaction product species and their quantities.

Comparative Example 2

An experiment was carried out using an experimental setup as shown in FIG. 2. A Pyrex® glass tube 21 having an interior volume of 25 ml was charged with 1.0 g of chemical grade metallic silicon powder having an average particle size of 150 μm, 0.45 g of flaky copper powder having an average particle size of 75 μm and 0.05 g of flaky tin powder having an average particle size of 75 μm and closed with a silicone rubber plug 23. The tube was evacuated to a vacuum of lower than 0.1 Torr, after which 0.1 ml (0.11 g) of chlorobenzene was injected through the plug 23. The tube 21 was heated at 450° C. for one hour in a ring furnace 24 and then allowed to cool down. Then 5 ml of chloroform was injected, followed by 10 minutes of shaking. The interior was restored to atmospheric pressure. The reaction solution diluted with chloroform was filtered and quantitatively analyzed by gas chromatography. Table 2 shows reaction product species and their quantities.

TABLE 2

| | | | Reaction product species and quantities | | |
|---|---|---|---|---|---|
| | Catalyst | Amount of catalyst added (wt %) | Diphenyldichlorosilane (mg) | Phenyltrichlorosilane (mg) | Biphenyl (mg) |
| Example 1 | Sn | 2.6 | 3.60 | N.D. | N.D. |
| Comparative Example 1 | Sn (mechanical alloying) | 9.1 | 1.9 | N.D. | 0.02 |
| Comparative Example 2 | Cu (prior art) | 30.0 | 0.13 | N.D. | 3.10 |

N.D.: not detected

Example 2

Chemical grade metallic silicon powder having an average particle size of 50 μm (by Simcoa, low aluminum grade: Al 0.05%, Fe 0.23%, Ca 0.02%), 100 parts, was weighed and placed in a polyethylene bag, to which was added 12 parts of previously finely divided stannous chloride having an average particle size of 20 μm. The contents were thoroughly mixed. The tin-silicon precursor thus obtained was placed in a half-cut quartz boat having an outer diameter of 75 mm, which was closed with a quartz boat of the same size. The assembly was placed in a quartz tube having an inner diameter of about 80 mm, through which nitrogen gas was flowed for purging the interior with nitrogen. Thereafter, the quartz tube was heated to 500° C. and held for about 2 hours for reaction, obtaining a contact mass. In the course of heating, the occurrence of reducing reaction of the tin compound was confirmed by the formation of tetrachlorosilane. The resulting contact mass had a tin concentration of 7.0%.

The contact mass was admitted into a fluidized bed reactor having an inner diameter of about 75 mm and equipped with a stirrer, which was heated to an interior temperature of 450° C. Gaseous chlorobenzene was fed into the fluidized bed at a flow velocity of 2 cm/s. The product gas was condensed in a condenser. Table 3 shows the composition of a sample taken at the steady state of reaction.

Comparative Example 3

A mixture of 100 parts of chemical grade metallic silicon powder having an average particle size of 50 μm and 8 parts of tin powder having an average particle size of 75 μm was worked on a mechanofusion device AMS-Lab (Hosokawa Micron Co., Ltd.) until tin was fully attached to surfaces of metallic silicon particles. The resulting contact mass was admitted into a fluidized bed reactor having an inner diameter of about 75 mm and equipped with a stirrer, which was heated to an interior temperature of 450° C. Gaseous chlorobenzene was fed into the fluidized bed at a flow velocity of 2 cm/s. The product gas was condensed in a condenser. Table 3 shows the composition of a sample taken at the steady state of reaction.

Comparative Example 4

100 parts of chemical grade metallic silicon powder having an average particle size of 50 μm, 10 parts of copper powder having an average particle size of 75 μm, 1 part (catalytic amount) of zinc powder having an average particle size of 75 μm, and 0.1 part (catalytic amount) of tin powder having an average particle size of 75 μm were admitted into a fluidized bed reactor having an inner diameter of about 75 mm and equipped with a stirrer, which was heated to an interior temperature of 450° C. Gaseous chlorobenzene was fed into the fluidized bed at a flow velocity of 2 cm/s. The product gas was condensed in a condenser. Table 3 shows the composition of a sample taken at the steady state of reaction.

Comparative Example 5

100 parts of chemical grade metallic silicon powder having an average particle size of 50 μm, 6 parts of copper powder having an average particle size of 75 μm, and 0.1 part (catalytic amount) of tin powder having an average particle size of 75 μm were admitted into a fluidized bed reactor having an inner diameter of about 75 mm and equipped with a stirrer, which was heated to an interior temperature of 450° C. Gaseous chlorobenzene was fed into the fluidized bed at a flow velocity of 2 cm/s. The product gas was condensed in a condenser. Table 3 shows the composition of a sample taken at the steady state of reaction.

TABLE 3

|  | Catalyst | Diphenyldichlorosilane (wt %) | Phenyltrichlorosilane (wt %) | Biphenyl (wt %) |
|---|---|---|---|---|
| Example 2 | Sn | 35.1 | 1.8 | 0.05 |
| Comparative Example 3 | Sn | 19.4 | 2.3 | 0.05 |
| Comparative Example 4 | Cu + Zn + Sn | 13.8 | 10.3 | 1.1 |
| Comparative Example 5 | Cu + Sn | 4.7 | 4.1 | 1.0 |

Japanese Patent Application No. 2004-304223 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for preparing a contact mass for use in the preparation of phenylchlorosilanes, comprising the steps of
   premixing
      metallic silicon and
      a tin compound selected from the group consisting of a tin halide, a tin nitrate, a tin sulfate, a tin organic acid salt, and a mixture thereof in a weight ratio that provides 0.1 to 50 parts by weight of metallic tin per 100 parts by weight of metallic silicon and
      0 to 20 parts by weight of a co-catalyst, selected from the group consisting of zinc, antimony, arsenic, and phosphorus and compounds and alloys thereof, per 100 parts by weight of metallic silicon,
      with the proviso that the amount of the co-catalyst is smaller than the amount of tin, and
      with the proviso that copper is included as an incidental impurity in the metallic silicon and the catalyst in an amount of 0 to less than 0.05% by weight based on the metallic silicon, and
   heat treating the premix in an inert gas atmosphere at a temperature of from 300° C. to 600° C. for from 1 to 10 hours.

2. The method of claim 1, which comprises premixing silicon powder, having an average particle size of 50 μm and containing 0.05% aluminum, 0.23% iron, and 0.02% calcium, and stannous chloride, having an average particle size of 20 μm.

3. The method of claim 1, which comprises premixing metallic silicon and stannous chloride in a weight ratio of 5 to 12 parts by weight of stannous chloride per 100 parts by weight of metallic silicon.

4. The method of claim 1, which comprises heat treating the premix in an inert gas atmosphere at a temperature of 500° C. for about 2 hours.

5. A method for preparing a contact mass for use in the preparation of phenylchlorosilanes, comprising the steps of
premixing
  metallic silicon and
  a tin compound selected from the group consisting of a tin halide, a tin nitrate, a tin sulfate, a tin organic acid salt, and a mixture thereof in a weight ratio that provides 0.1 to 50 parts by weight of metallic tin per 100 parts by weight of metallic silicon and
  0.05 to 5 parts by weight of a co-catalyst, selected from the group consisting of zinc, antimony, arsenic, and phosphorus and compounds and alloys thereof, per 100 parts by weight of metallic silicon,
  with the proviso that the amount of the co-catalyst is smaller than the amount of tin, and
  with the proviso that copper is included as an incidental impurity in the metallic silicon and the catalyst in an amount of 0 to less than 0.05% by weight based on the metallic silicon, and
heat treating the premix in an inert gas atmosphere at a temperature of from 300° C. to 600° C. for from 1 to 10 hours.

6. The method of claim 1, wherein the amount of copper is 0% by weight.

7. The method of claim 5, wherein the amount of copper is 0% by weight.

8. The method of claim 1, wherein the tin compound is used in an amount of 3.13 to 50 parts by weight of metallic tin per 100 parts by weight of metallic silicon.

9. The method of claim 5, wherein the tin compound is used in an amount of 3.13 to 50 parts by weight of metallic tin per 100 parts by weight of metallic silicon.

* * * * *